United States Patent [19]

Klibanov et al.

[11] 4,414,147

[45] Nov. 8, 1983

[54] METHODS OF DECREASING THE HYDROPHOBICITY OF FIBROBLAST AND OTHER INTERFERONS

[75] Inventors: Alexander M. Klibanov, Boston; Robert S. Langer, Cambridge, both of Mass.

[73] Assignee: Massachusetts Institute of Technology, Cambridge, Mass.

[21] Appl. No.: 255,321

[22] Filed: Apr. 17, 1981

[51] Int. Cl.$^3$ .............................................. C07G 7/00
[52] U.S. Cl. ............................ 260/112 R; 260/112 B; 424/85
[58] Field of Search ..................... 260/112 R, 112 B; 424/85

[56] References Cited

U.S. PATENT DOCUMENTS 4,061,538 12/1977 Dorner .................................. 195/29

OTHER PUBLICATIONS

Stewart et al., Proc. Natl. Acad. Sci., USA, vol. 74, No. 10, pp. 4200–4204, 1977.
Mizrahi et al., J. Biol. Chem., vol. 253, No. 21, pp. 7612–7615, 1978.
Inglot et al., Arch Immunol Ther. Exp., vol. 28 (2) p. 313–322, 1980–Abst.
Inglot et al., Arch. Virol., vol. 60 (1), pp. 43–50, 1979–Abst.
Bose et al., J. Biol. Chem., vol. 251, No. 6, pp. 1659–1662, 1976.
Bose et al., J. Biol. Chem., vol. 252, No. 23, pp. 8336–8337, 1977.
Vilcek et al., J. Clin. Micro., vol. 11, No. 1, pp. 102–105, Jan. 1980.

Primary Examiner—John C. Bleutge
Assistant Examiner—Patricia Short
Attorney, Agent, or Firm—Arthur A. Smith, Jr.; David E. Brook

[57] ABSTRACT

A method for improving the stability and usefulness of interferon, including human fibroblast interferon, is disclosed. In this method, interferon is bonded to a non-hydrophobic substance to create a molecular complex that is less hydrophobic than untreated interferon.

3 Claims, No Drawings

METHODS OF DECREASING THE HYDROPHOBICITY OF FIBROBLAST AND OTHER INTERFERONS

TECHNICAL FIELD

This invention is in the fields of cell biology immunology, medicine and pharmacology.

BACKGROUND ART

Interferon is a biochemical that is produced and released by animal and human cells in response to viral infection. It constitutes one of the major defense mechanisms against viral infections in mammals, including humans. In addition to its antiviral functions, research indicates that interferon has immunoregulatory properties, effects upon various cellular functions including cell division, and value as an anticancer agent.

There are at least three distinct types of human interferon. Leukocytes and other lymphoid cells produce leukocyte interferon, commonly designated as L-interferon, Le-interferon, or α-interferon. Fibroblast and other nonlymphoid cells produce fibroblast interferon, commonly designated as F-interferon or β-interferon. A third category of interferon is commonly known as immune interferon, T-interferon, or γ-interferon. See, e.g., Vilcek, J. et al., "Synthesis and Properties of Various Human Interferons," *Microbiology*-1980, Amer. Soc. for Microbiology, pp. 204–207 (1980).

F-interferon is produced and released in very minute quantitites by in vivo fibroblast cells (and, to a lesser extent, by lymphoid cells) in response to viral infections. In addition, F-interferon can be produced in vitro by cultures of fibroblast cells. Researchers have developed several methods of stimulating such cells to produce abnormally high quantities of F-interferon. See, e.g. Billiau, A. et al., "Mass production of human interferon in diploid cells stimulated by poly I:C," *Journal Gen. Virol.* 19:1–8 (1973); Havell, E. A. et al., "Production of high-titered interferon in cultures of human diploid cells," *Antimicrob. Ag. Chemother.* 2:476–484 (1972); Ho, M. et al., "Accentuation of production of human interferon by metabolic inhibitors," *Proc. Soc. Exp. Biol. Med.* 139:259–262 (1972). However, some problems still inhibit the effective use of F-interferon in biomedical research and treatment.

One important characteristic that decreases the usefulness of F-interferon is its hydrophobicity. In general, a hydrophobic substance within an aqueous or biological solution will tend to adopt configurations that minimize the area of contact between the substance and the solution. Hydrophobic substances in aqueous or biological solutions tend to form globules, and to cling to substrates such as filters and cell walls. This reduces the ability of the substance to be absorbed by and transported within an animal or human body or tissue culture.

As normally produced by fibroblast cells in vitro, F-interferon tends to become attached to and surrounded by carbohydrate groups and possibly other types of non-polar hydrophobic moieties. Such carbohydrate moieties may be natural and indigenous constituents of interferon molecules, rather than merely impurities and contaminants. However, research performed to date indicates that F-interferon retains some or all of its beneficial properties and effectiveness if carbohydrate moieties are removed from the remaining interferon molecule.

Early research indicated that injections of sizable quantities of fibroblast interferon produce very small quantities of F-interferon in the blood serum of animals and humans. See Billiau, A. et al., "Human Fibroblast Interferon for Clinical Trials: Pharmacokinetics and Tolerability in Experimental Animals and Human," *Antimicrob. Ag. Chemother.* 16:56–63 (1979); Edy, V. G. et al., "Non-appearance of Injected Fibroblast Interferon in Circulation," *Lancet* 1:451–452 (1978). Clearance of F-interferon from the bloodstream of an injected animal or human may be partially responsible for small quantities of F-interferon being detected in the bloodstream after injection. See Cantell, K. et al., "Pharmacokinetics of Human Leukocyte Interferon," *J. Inf. Dis.* 133:A6–A12 (1976). Inactivation by animal or human blood also may be partially responsible for small quantities of F-interferon being detected in the bloodstream after injection. See Cesario, T. C. et al., "Inactivation of Human Interferon by Body Fluids," *Tex. Rep. Biol. Med.* 35:443–448 (1977). However, research indicates that clearance and inactivation probably are not the primary reasons why fibroblast interferon is poorly absorbed into the bloodstream after intramuscular injection. See Vilcek, J. et al., "Pharmacokinetic Properties of Human Fibroblast and Leukocyte Interferon in Rabbits," *Journal of Clinical Microbiology* 11:102–105 (1980). This research implies that the problem of low postinjection serum activity is caused primarily by the tendency of fibroblast interferon to cling to tissue at the site of injection, which in turn appears to be caused by the hydrophobicity of fibroblast interferon.

Carbohydrate and other hydrophobic moieties also cause or exacerbate various other problems in producing, storing, and using fibroblast interferon, in addition to the problem of low serum activity after injection. For example, numerous types of molecules and enzymes react with carbohydrates to form various by-products. Therefore, carbohydrate moieties may tend to reduce the stability and longevity of fibroblast interferon, both in vivo and in vitro during its production, storage, and use.

In addition, hydrophobic impurities and contaminants within an aqueous or biological solution containing fibroblast interferon will tend to mix with and adhere to the interferon, rendering it impure and interfering with its desirable properties. Adverse reactions, including fever and nausea, by patients injected with impure interferon have already been noted by researchers. See, e.g., Billiau, A. et al., "Human Fibroblast Interferon for Clinical Trials: Pharmacokinetics and Tolerability in Experimental Animals and Humans," *Antimicrob. Agents and Chemotherapy* 16:46–63 (1979).

Other problems caused by the relative reactivity of moieties on interferon are likely to become apparent during research and medical usage involving interferon. Any such problems are likely to be alleviated or eliminated by treatment of the interferon to remove or modify such moieties.

DISCLOSURE OF THE INVENTION

This invention relates to the chemical treatment and modification of hydrophobic interferon, such as human fibroblast interferon. It has been discovered that chemical modification of interferon increases its ability to pass through a filter in the presence of aqueous solutions. It is believed that such modification increases the solubility of interferon in aqueous and biological solutions, thereby increasing the ability of interferons to be absorbed into and transported within an animal body or biological system.

These useful improvements are achieved by reacting interferon with certain substances to form molecular complexes. These complexes are less hydrophobic than untreated interferon, yet they retain some or all of the useful biochemical properties of the interferon.

BEST MODE OF CARRYING OUT THE INVENTION

This invention discloses several embodiments of the procedures used to create such molecular complexes. A first embodiment involves contacting interferon with a suitable oxidizing agent, such as sodium periodate ($NaIO_4$). The oxidizing agent reacts with carbohydrate moieties on the interferon to create relatively reactive groups, such as aldehydes, which are attached to the interferon. The reaction can occur in several ways. The following formula indicates one such chemical reaction:

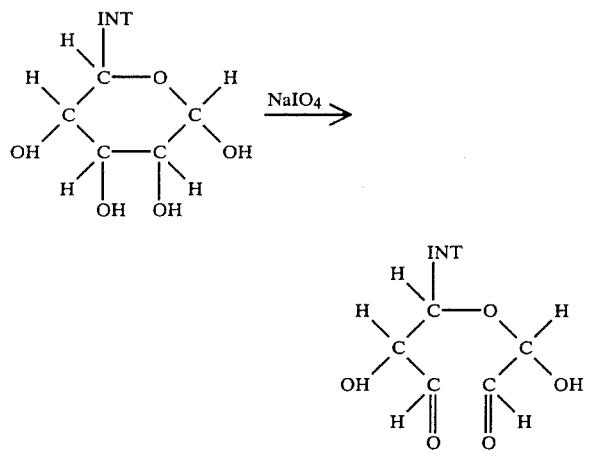

where INT represents the remainder of the interferon molecule.

The treated inteferon is then contacted with a suitable non-hydrophobic substance, such as an amino acid that is added to the interferon solution. The reactive groups of the treated interferon react with the amino acid or other non-hydrophobic substance to bond the interferon to that substance. The following formula indicates such a reaction:

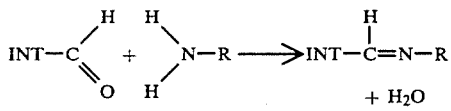

where INT represents the remainder of the interferon molecule and R represents the remainder of an amino acid. The result is a molecular complex comprising a non-hydrophobic substance covalently bonded to interferon.

The second embodiment of this invention involves contacting a non-hydrophobic substance, such as cationic DEAE dextran, with a suitable oxidizing agent, such as sodium periodate. The oxidizing agent reacts with the non-hydrophobic substance to create relatively reactive groups, such as aldehydes, which are attached to the substance. The following formula indicates one such chemical reaction:

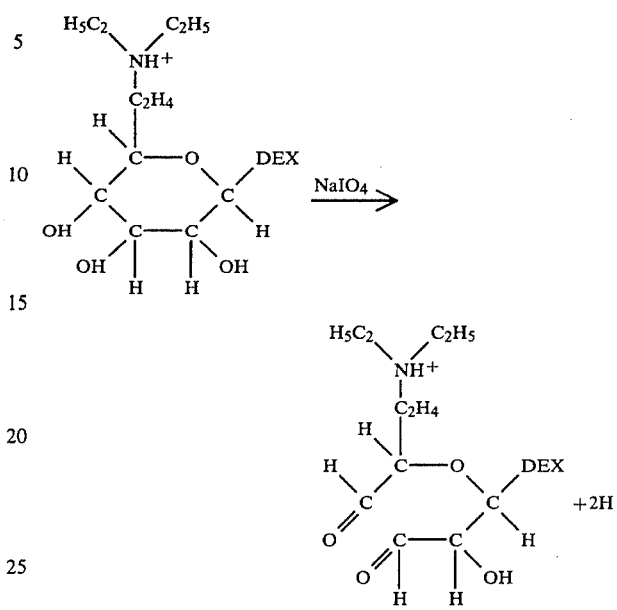

where DEX represents the remainder of a DEAE dextran molecule. This modified non-hydrophobic substance is then contacted with interferon. The reactive groups of the non-hydrophobic substance react with the interferon to bond the non-hydrophobic substance to the interferon. The following formula indicates one such reaction:

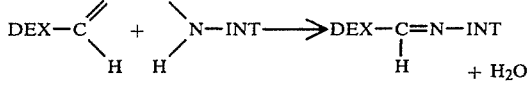

where INT represents the remainder of the interferon molecule and DEX represents the remainder of the cationic DEAE dextran molecule. The result is a molecular complex comprising DEAE dextran covalently bonded to fibroblast interferon.

A variety of non-hydrophobic substances can be used in either of the foregoing embodiments of this invention. The inventors have achieved favorable results by linking each of the following substances to fibroblast interferon: dextran, diethyl-amino-ethyl dextran, carboxymethylcellulose, and sodium alginate. Other suitable non-hydrophobic substances can be determined by those skilled in the art using no more than routine experimentation.

A third embodiment of this invention would use, as the non-hydrophobic substance, various types of molecules which occur naturally within most nonhomogenized biological solutions. Most biological solutions, such as blood serum or lymph, are complex mixtures of a variety of molecular components, including proteins such as albumin. It is possible to reduce the hydrophobicity of interferon by bonding it to a non-hydrophobic molecule such as albumin which occurs naturally within the biological solution that contains the interferon. Such a reaction would eliminate the need to add a non-hydrophobic substance, such as an exogenous amino acid, to the interferon solution.

A fourth embodiment of this invention involves adding a non-hydrophobic substance, such as an exogenous amino acid, to a solution that contains interferon. The two chemicals are allowed to mix, then an oxidizing agent such as sodium periodate is added to the solution. In this embodiment, the oxidizing agent may oxidize molecules of both interferon and the non-hydrophobic substance, allowing them to become bonded to each other.

Any of several oxidizing agents can be used in any of the foregoing embodiments of this invention. In general, any oxidizing agent that creates relatively reactive moieties such as aldehydes either on carbohydrate-containing interferon, or on any non-hydrophobic substance used for the purposes described above, is suitable so long as it does not destroy the useful biochemical properties of the interferon or the non-hydrophobic substance. In addition, radiation of interferon with electromagnetic energy or other physical processes may be regarded as treatment with an oxidizing agent if such processes accomplish the purposes described herein. Such suitable oxidizing agents may be determined by those skilled in the art using no more than routine experimentation.

A fifth embodiment of this invention involves chemical modification of interferon by reacting it with certain reagents, such as dicarboxylic anhydrides. Reagents that can be used for this purpose include succinic anhydride, maleic anhydride, and copoly(ethylene maleic anhydride) (PEMA). These reagents become attached to the interferon through chemical reactions such as acylation. The following formula indicates one such reaction:

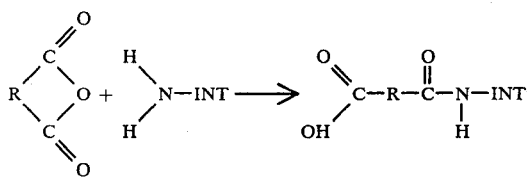

where R represents an organic group and INT represents the remainder of the interferon molecule. The result is a molecular complex comprising at least one relatively hydrophilic organic group covalently bonded to interferon.

This invention is not limited to the treatment of fibroblast interferon. Although research indicates that F-interferon is more hydrophobic than either L-interferon or T-interferon, both L-interferon and T-interferon appear also to have carbohydrate and other moieties attached to them. Replacement or alteration of these moieties on L-interferon and T-interferon is likely to decrease their hydrophobicity and improve their stability and effectiveness by using the same biochemical principles, reactions and techniques that are described above regarding fibroblast interferon.

The term "non-hydrophobic substance" is used broadly herein, as a convenient notation to indicate any substance that is less hydrophobic than interferon. In addition, the hydrophobicity of the unreacted substance is not important, as long as the reaction product is less hydrophobic than untreated interferon.

This invention is not limited to interferon that is produced by, or used to treat, human cells and human bodies. Research indicates that interferon is produced and utilized by many types of mammals, and that apparently all types of interferon have carbohydrate moieties attached. In addition, interferon produced by a given species of mammal is sometimes used in research involving other species of mammals. Replacement or alteration of carbohydrate or hydrophobic moieties on any type of interferon is likely to decrease its hydrophobicity and improve its stability, effectiveness, and usefulness as a research and medical tool, by using the same biochemical principles and reactions that are described above.

Additionally, this invention is not limited to interferon that is produced by naturally occurring cells. Research is proceeding rapidly on the splicing and alteration of DNA, genes, plasmids and chromosomes within bacterial and other cells. It is also possible that scientists will learn to synthesize interferon by chemical reactions. Similarly, the term interferon should be construed broadly to include derivatives and byproducts of interferon and similar functionally equivalent substances. If interferon of any origin or derivation contains or is attached to carbohydrate, hydrophobic, or relatively reactive moieties that cause or exacerbate problems of the type contemplated by this invention, then the methods disclosed by this invention can be used with beneficial effect to reduce the hydrophobicity, instability and contamination of such interferon.

In its broadest sense, this invention relates to increasing the usefulness of interferon by reducing its hydrophobicity. The inventors have disclosed numerous specific procedures and reagents for accomplishing such results. Although the experimental work done to date has involved bonding interferon to less hydrophobic substances, it would be clear to someone skilled in the art that the hydrophobicity of interferon can be reduced by altering, or eliminating entirely, hydrophobic moieties that are attached to interferon. Such processes, and the compositions of matter that result from such processes, are within the teachings and the claims of this invention.

EXAMPLES

Example 1: Untreated Interferon

Human fibroblast interferon was supplied by the Cell Culture Center of the Massachusetts Institute of Technology. The interferon was produced by a cell line (FS-4) from human foreskin using a modified superinduction procedure involving poly I-poly C. Crude interferon fluids containing Dulbecco's Modified Eagle Medium (DMEM) and a small amount of plasma protein were frozen at $-70°$ C. prior to use. The undiluted solution contained 14,000 units/ml, as measured by a procedure described by Havell and Vilcek, ("production of High Titered Interferon in Cultures of Human Diploid Cells" *Journal of Antimicrobial Agents and Chemotherapy* 2:6 p. 476–484 (December, 1972)). This procedure consisted of the following:

Two-fold serial dilutions were made in microtiter plates using medium consisting of DMEM plus 5% fetal bovine serum. FS-4 cells were mixed with the interferon dilutions, and incubated for 20–24 hours at 37° C. Each well was then challenged with 1,000 plaque forming units of vesicular stomatitis virus. After 48–72 hours, each well was visually assessed semi-quantitatively. The concentration of interferon in each sample was indicated by the greatest dilution at which the FS-4 cells were given 50% protection from the virus. All interferon samples were assayed in this way.

A 1-ml sample of interferon (14,000 units) was diluted with 2 ml of 0.3 molar phosphate buffer solution, with a pH of 7.3. One ml of this solution was passed through a 0.45 μm filter composed of a mixed ester of cellulose acetates and nitrates in a polyvinyl chloride casing (Millex-HA, Millipore Corporation, Bedford, MA). As indicated in Table I, approximately 3% to 6% of the interferon passed through the filter.

Example 2: Interferon With Treated Dextran

One ml of DEAE dextran with 0.3 molar phosphate buffer was added to one ml of 0.1 molar $NaIO_4$. After 60 minutes, 1 ml of 14,000 units/ml of human fibroblast interferon, prepared as described in Example 1, was added to the treated dextran solution. After 60 minutes, 0.027 gram of glucose was added to the mixture to scavenge any unreacted $NaIO_4$. After 15 minutes, a portion of this solution was passed through a 0.45 μm filter as described above. One ml each of the filtered and unfiltered solution were assayed as described in Example 1. As indicated in Table 1, approximately 25% of the treated interferon passed through the filter.

Example 3: Interferon with Succinic Anhydride

Three ml of buffered interferon solution were prepared as described in Example 1. Two mg of succinic anhydride were added to the solution, and allowed to react for 60 minutes. A portion of the solution was passed through a 0.45 μm filter. One ml each of the filtered and unfiltered solution were assayed for interferon activity, using the methods described in Example 1. As indicated in the table, virtually all of the interferon that was treated with succinic anhydride passed through the filter. The data, which indicate that slightly more interferon was present in the filtered solution than in the unfiltered solution, are within the range of experimental accuracy of the assay.

TABLE I

Amounts of Fibroblast Interferon That Passed Through a 0.45 μm Filter

| | Interferon Activity | | |
|---|---|---|---|
| | Unfiltered | Filtered | % |
| Control (phosphate buffer only) | 6200 | 200 | 3% |
| Control (phosphate buffer only) | 2450 | 145 | 6% |
| Treated (DEAE dextran, $NaIO_4$) | 3100 | 780 | 25% |
| Treated (succinic anhyride) | 1200 | 1450 | 121% |

Industrial Applicability

The invention described herein is useful in the treatment of fibroblast interferon to reduce its hydrophobicity. Such treatment can improve the usefulness of fibroblast interferon as an anti-viral agent, immunoregulatory agent, and anti-cancer agent, primarily by increasing the rates at which it is absorbed and transported within animal and human bodies, biological cultures, and research environments.

This invention is also useful in reducing other problems relating to the production, storage, usage and biochemical properties of fibroblast interferon. Carbohydrate, hydrophobic, and reactive moieties on fibroblast interferon tend to promote its contamination and decomposition. In addition, impurities on fibroblast interferon apparently cause or promote adverse reactions such as fever and nausea in animals and humans. Modification, replacement or elimination of such moieties will allow researchers and users to isolate, identify, evaluate, resolve and avoid such problems.

In addition, reducing the hydrophobicity of fibroblast interferon will allow new techniques to handle and purify it. For example, untreated fibroblast interferon tends to cling to nearly any type of substrate, including filters and adsorbents. This causes filtration and adsorption to be impractical as methods of purifying and sterilizing fibroblast interferon. Reducing the hydrophobicity of interferon will increase the range of techniques, such as filtration and adsorption, that can be used to purify and handle fibroblast interferon.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of reducing the hydrophobicity of interferon, comprising contacting said interferon with an anhydride of a dicarboxylic acid under conditions that allow said interferon to become bonded to said anhydride.

2. A method of claim 1 wherein said anhydride is selected from the following group: succinic anhydride, maleic anhydride, poly(ethylene maleic anhydride), and poly(ethylene succinic anhydride).

3. A composition of matter comprising a molecule of interferon that is bonded to an anhydride of a dicarboxylic acid.

* * * * *